US00PP18983P2

(12) United States Plant Patent
Hanes

(10) Patent No.: US PP18,983 P2
(45) Date of Patent: Jun. 24, 2008

(54) ***VERBENA* PLANT NAMED 'LAN UPMAG'**

(50) Latin Name: *Verbena hybrida*
Varietal Denomination: Lan Upmag

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/709,459

(22) Filed: Feb. 22, 2007

(51) Int. Cl.
*A01H 5/00* (2006.01)

(52) U.S. Cl. ..... Plt./308
(58) Field of Classification Search ..... Plt./308
See application file for complete search history.

*Primary Examiner*—Kent L Bell
(74) *Attorney, Agent, or Firm*—Jondle & Associates, P.C.

(57) ABSTRACT

A *verbena* cultivar particularly distinguished by its magenta colored flowers, vigorous and free branching, an upright and semi-compact growth habit in the early stages and becoming slightly spreading and decumbent and tolerance to powdery mildew, is disclosed.

2 Drawing Sheets

Genus and species: *Verbena hybrida.*
Variety denomination: 'Lan Upmag'.

BACKGROUND OF THE NEW PLANT

The present invention comprises a new and distinct cultivar of *verbena,* botanically known as *Verbena hybrida,* and hereinafter referred to by the cultivar name 'Lan Upmag'. The new cultivar originated in 2003 in Gilroy, Calif. from the self-pollination of '1655-2', an unpatented dark red flowered proprietary *verbena.*

The seeds produced by the self-pollination were sown in June 2003. A single plant selection was chosen for further evaluation and for asexual propagation in September 2003.

The new cultivar was created in 2003 in Gilroy, Calif. and has been asexually reproduced repeatedly by vegetative cuttings and tissue culture in Gilroy, Calif. and Andijk, The Netherlands over a three-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar have been applied for in Switzerland on Oct. 30, 2006.

SUMMARY OF THE INVENTION

The following are the most outstanding and distinguishing characteristics of the new cultivar when grown under normal horticultural practices in Gilroy, Calif. and Andijk, The Netherlands.

1. Magenta flower color;
2. Upright and semi-compact plant growth habit in the early stages and becoming slightly spreading and decumbent;
3. Vigorous and free branching; and
4. Tolerance to powdery mildew

DESCRIPTION OF THE PHOTOGRAPHS

This new *verbena* plant is illustrated by the accompanying photographs which show overall plant habit, including blooms, buds and foliage of the plant. The plants were approximately 9 to 10 weeks old, grown in a greenhouse in Hillscheid, Germany in May 2006. The colors shown are as true as can be reasonably obtained by conventional photographic procedures.

Figure 1:
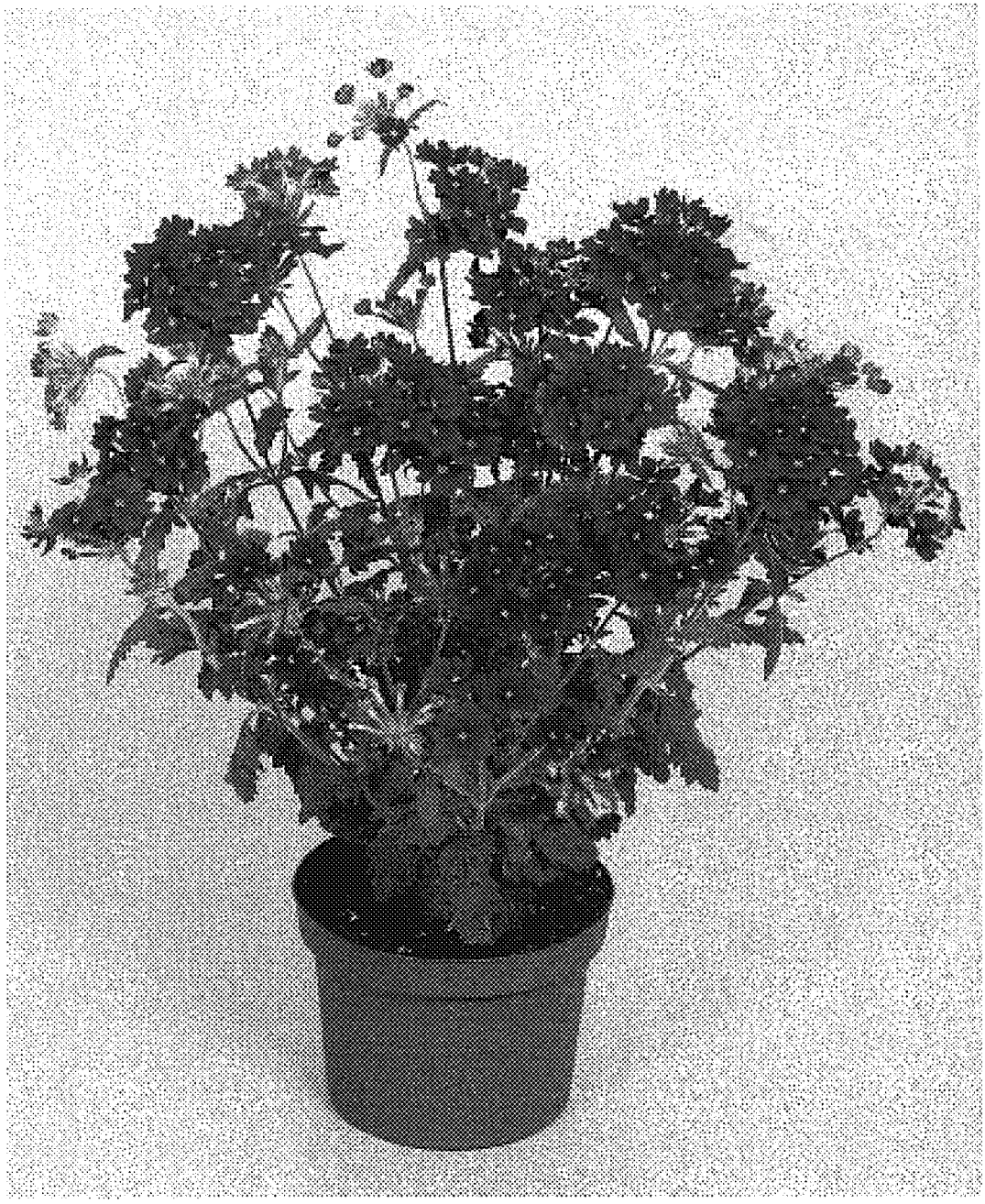

FIG. 1. shows the overall plant habit, including blooms, buds and foliage of the plant.

Figure 2:
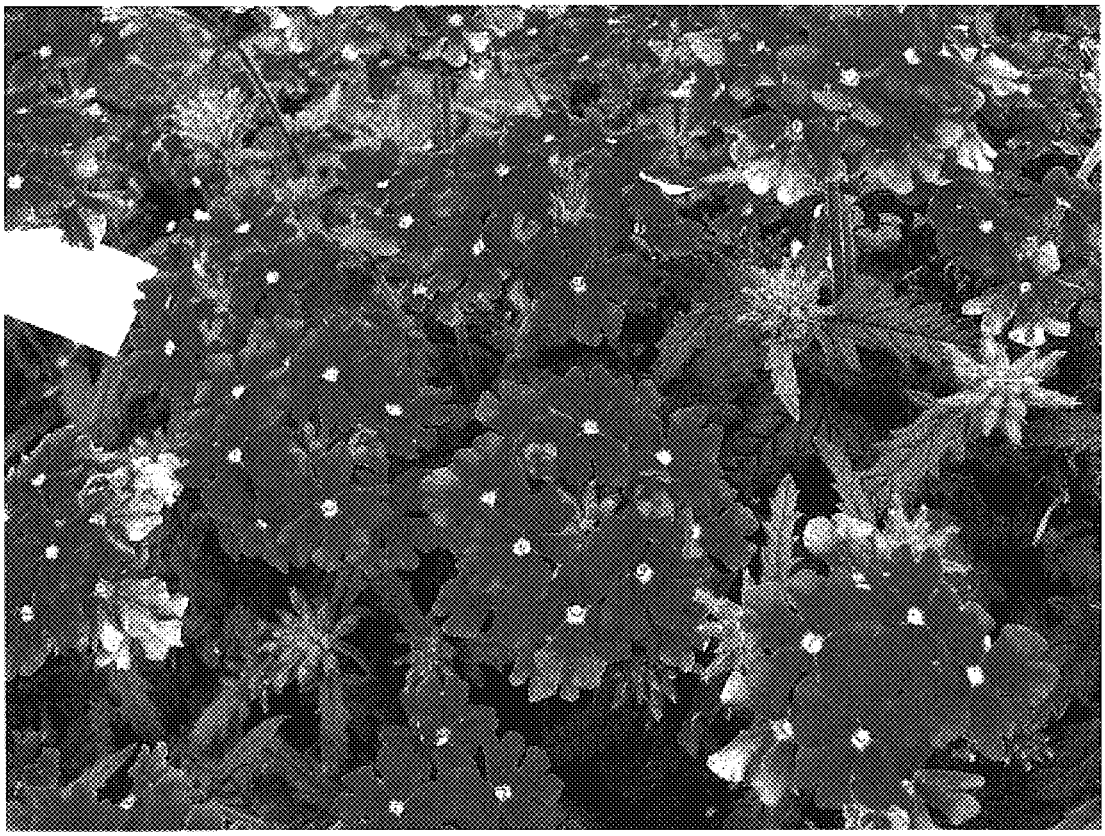

FIG. 2. shows a close-up of the mature inflorescence of the plant.

DESCRIPTION OF THE NEW CULTIVAR

The following detailed descriptions set forth the distinctive characteristics of 'Lan Upmag'. The data which define these characteristics were collected from asexual reproductions carried out in Gilroy, Calif. The plant history was taken from plants approximately 20 to 24 weeks old, grown in 6-inch pots in Gilroy, Calif. The plants had one plant growth regulator treatment and one terminal pinch after cuttings were transplanted from 4-inch pots to 6-inch pots. Color readings were taken in a greenhouse under natural light. Color references are primarily to the RHS Colour Chart of The Royal Horticultural Society of London (R.H.S.) (2001 edition). Texture description details were observed with a dissecting microscope.

DETAILED BOTANICAL DESCRIPTION

Classification:
*Botanical.—Verbena hybrida.*
*Common name.—Verbena.*

Parentage: Self-pollination of '1665-2' a proprietary *verbena* plant having dark red flowers (unpatented).

Growth:
*Form.*—Herbaceous annual; mostly upright growth in the early stages and semi-compact and then becoming slightly spreading and decumbent plant habit.
*Growth and branching habit.*—Vigorous and free-branching with multiple secondary lateral branches.
*Height* (*measured from the top of the soil, including flowers*).—23.0 cm to 30.0 cm.
*Width* (*horizontal plant diameter*).—46.0 cm to 50.0 cm.

*Time to produce a finished flowering plant.*—Approximately 9 weeks for a 12-cm pot in the spring.

*Outdoor plant performance.*—Use in containers and hanging baskets.

*Time to initiate and develop roots.*—Approximately 7 to 10 days at 22 to 24 degree Celsius.

*Root description.*—Fibrous, fleshy, white.

Leaves:

*Arrangement.*—Opposite.

*Immature leaf.*—Color: Upper surface: RHS 137B. Lower surface: RHS 137C.

*Mature leaf.*—Color: Upper surface: RHS 137B. Lower surface: RHS 137C. Length: 4.0 cm to 4.5 cm. Width: 2.4 cm to 2.8 cm. Shape: Ovate. Apex: Acute. Base: Attenuate. Margin: Irregular, crenately incised. Texture: Hirsute, hispid. Venation: Palmate. Venation color: RHS 145A.

*Petioles.*—Length: 0.5 cm to 0.7 cm. Diameter: 0.15 cm. Color: RHS 145A. Texture: Hirsute; pilose with a few glandular hairs.

Stems:

*Number of branches per plant.*—25 to 35.

*Color.*—RHS 144A.

*Length.*—25.0 cm to 30.0 cm.

*Diameter.*—0.2 cm.

*Internode length.*—2.0 cm to 3.5 cm.

*Texture.*—Hirsute; hispid, a few glandular hairs.

*Stem anthocyanin.*—Absent.

Flower buds:

*Color* (*at tight bud*).—RHS 61A.

*Shape.*—Tubular.

*Diameter.*—0.2 cm.

*Length.*—1.8 cm to 2.0 cm.

Inflorescence:

*Blooming habit.*—Flowers continuously from spring through fall; flowers appear about 9 to 10 weeks after planting of rooted cuttings.

*Lastingness of individual blooms on the plant.*—6 to 7 days.

*Fragrance.*—None.

*Inflorescence type.*—Terminal raceme.

*Horizontal diameter of inflorescence.*—5.0 cm to 6.0 cm.

*Vertical diameter of inflorescence.*—3.0 cm to 3.5 cm.

*Number of florets per raceme.*—14 to 20.

*Peduncle.*—Color: RHS 144A. Diameter: 0.15 cm. Length: 7.0 cm to 8.0 cm. Texture: Hirsute; less hispid than stem; glandular hairs.

Flowers:

*Floret form.*—Salverform; sessile on raceme.

*Floret diameter.*—2.0 cm to 2.4 cm.

*Number of petals and arrangement.*—Each floret is composed of 5 petals fused at the base.

*Immature flower.*—Color: Upper surface: Closest to RHS N57A but deeper; is more red in tone and a little more velvety red than the mature flowers. Lower surface: RHS N155B basally; increasing in intensity to RHS 61B at the margins.

*Mature flower.*—Color: Upper surface: Closest to RHS N57A but deeper and more red in tone. Lower surface: RHS N155B basally; increasing in intensity to RHS 61B at the margins.

*Corolla.*—Color tube color (inside): Closest to RHS N155D. Tube length: 2.3 cm to 2.4 cm.

*Petals.*—Size: Length: 0.7 cm to 0.8 cm. Width: 0.7 cm to 1.0 cm. Lobe shape: Obovate. Apex: Emarginate. Base: Fused. Margin: Entire. Texture: Upper surface: Papillose. Lower surface: Pilose, papillose.

*Calyx.*—General: Composed of five sepals whose margins are fused to each other along their length, with a transparent membrane of less than 0.1 cm in width, with one smaller sepal (0.6 cm) attached to the base of the calyx. Color: RHS 138A for the outer surface; inner surface was not observed. Length 1.2 cm to 1.3 cm. Width: 0.2 cm to 0.3 cm. Shape: Linear. Apex: Acute. Base: Fused. Margin: Entire. Texture: Hirsute; glandular hairs, some with a magenta-red hue.

Reproductive organs:

*Stamens.*—Anthers and filaments fused to upper half of corolla tube.

*Anther quantity.*—Four with two pollen sacs per anther.

*Anther length.*—0.1 cm.

*Pollen.*—Amount: Moderate. Color: RHS 1A.

*Pistil.*—One.

*Style length.*—1.8 cm to 2.0 cm.

*Style color.*—RHS 144A.

*Stigma color.*—RHS 144A.

Fruit/Seed set: Have not been observed.

Disease and insect resistance: Tolerant to powdery mildew.

COMPARISON WITH PARENTAL AND COMMERCIAL CULTIVARS

'Lan Upmag' differs from the proprietary, selfing parent '1655-2' (unpatented) in that 'Lan Upmag' has magenta flowers, while '1655-2' has dark red flowers. Additionally, 'Lan Upmag' has a more compact and has an upright plant habit and darker foliage than '1655-2'.

'Lan Upmag' differs from the commercial variety 'Lan Chered' (U.S. Plant Pat. No. 15,602) by having a more upright plant habit with some spreading while 'Lan Chered' has a plant habit with more spreading. Additionally, 'Lan Upmag' has a lighter foliage color and longer peduncles than 'Lan Chered'.

I claim:

1. A new and distinct cultivar of *verbena* plant as shown and described herein.

* * * * *